United States Patent
Maki et al.

(10) Patent No.: US 10,806,639 B2
(45) Date of Patent: Oct. 20, 2020

(54) DISPOSABLE WEARING ARTICLE

(71) Applicant: Unicharm Corporation, Shikokuchuo-shi, Ehime (JP)

(72) Inventors: Hideaki Maki, Kanonji (JP); Shunsuke Takino, Kanonji (JP); Takuya Inoue, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 361 days.

(21) Appl. No.: 15/740,848

(22) PCT Filed: May 17, 2016

(86) PCT No.: PCT/JP2016/064569
§ 371 (c)(1),
(2) Date: Dec. 29, 2017

(87) PCT Pub. No.: WO2017/002469
PCT Pub. Date: Jan. 5, 2017

(65) Prior Publication Data
US 2018/0200122 A1     Jul. 19, 2018

(30) Foreign Application Priority Data
Jun. 30, 2015   (JP) ................................ 2015-132233

(51) Int. Cl.
*A61F 13/15*  (2006.01)
*A61F 13/49*  (2006.01)
(Continued)

(52) U.S. Cl.
CPC ...... *A61F 13/49012* (2013.01); *A61F 13/496* (2013.01); *A61F 13/49011* (2013.01);
(Continued)

(58) Field of Classification Search
CPC .............. A61F 13/49012; A61F 13/494; A61F 13/496; A61F 13/4902; A61F 2013/49033; A61F 2013/49041
(Continued)

(56) References Cited

U.S. PATENT DOCUMENTS 5,593,401 A * 1/1997 Sosalla ............. A61F 13/49011
604/385.28
2005/0010184 A1    1/2005 Klemp et al.
(Continued)

FOREIGN PATENT DOCUMENTS

JP    2002-248127 A    9/2002
JP    2010-227152 A   10/2010
(Continued)

OTHER PUBLICATIONS

International Search Report in PCT/JP2016/064569, datd Jul. 19, 2016. 5pp.

*Primary Examiner* — Jacqueline F Stephens
(74) *Attorney, Agent, or Firm* — Hauptman Ham, LLP (57) ABSTRACT

Disclosed is a disposable wearing article in which a front waist region has an appropriate retaining force and free from a possibility that the lower abdominal region may be tightened. On a body facing surface, an elastic strip extending in a lateral direction between both lateral edges is located along a lower edge area of a front waist region of the disposable wearing article.

15 Claims, 9 Drawing Sheets

(51) Int. Cl.
*A61F 13/494* (2006.01)
*A61F 13/496* (2006.01)

(52) U.S. Cl.
CPC .. *A61F 13/49019* (2013.01); *A61F 13/49061* (2013.01); *A61F 13/49413* (2013.01)

(58) Field of Classification Search
USPC ............ 604/385.24, 385.25, 385.26, 385.27, 604/385.28, 385.29, 385.3, 385.31
See application file for complete search history.

(56) References Cited

U.S. PATENT DOCUMENTS

2012/0022482 A1   1/2012   Nakajima et al.
2012/0259307 A1   10/2012   Otsubo et al.

FOREIGN PATENT DOCUMENTS

JP          2011-156341 A    8/2011
JP          2015-73636 A     4/2015

\* cited by examiner

DISPOSABLE WEARING ARTICLE

RELATED APPLICATIONS

The present application is a National Phase of International Application Number PCT/JP2016/064569, filed May 17, 2016, which claims priority to Japanese Application Number 2015-132233, filed Jun. 30, 2015.

TECHNICAL FIELD

The present disclosure relates to disposable wearing articles such as disposable diapers and the like.

BACKGROUND ART

The patent literature 1 described below discloses a disposable wearing article including a front waist region, a rear waist region, a crotch region extending between the front and rear waist regions and a liquid absorbent structure extending to the front and rear waist regions centering on the crotch region.

CITATION LIST

Patent Literature

PTLA 1: Japanese Unexamined Patent Application Publication No. 2002-248127(JP2002-248127A)

SUMMARY OF INVENTION

Technical Problem

In the disposable wearing article disclosed in PTL 1, the front waist region is entirely arranged with a plurality of string-like or strand-like front waist elastic members extending in a lateral direction in a contractible manner under tension. In this way, the front waist region is elastically contractible in the lateral direction and a tensile stress thereof generates a body contact pressure ensuring the front waist region to fit on the wearer's body.

However, for example, when the wearer who is a few month old baby, excessive tightening on the lower abdominal region for the purpose of improving the fittablity often creates a feeling of discomfort against the wearer. In addition, when a tensile stress of a plurality of the front waist elastic members arranged on the lower edge area of the front waist region facing the lower abdominal region is relatively high, this may create a feeling of discomfort against the wearer. In particular, the few month old baby having the relatively delicate skin, reddish pressure marks may be left on the skin. Furthermore, the few month old baby sometimes assumes a supine posture such as putting the toe in the mouth while lifting both legs with the buttocks and holding the toe. In such peculiar posture, when the front waist region includes a plurality of front waist elastic members arranged in its front lower edge area, these front waist elastic members are brought together in this lower edge area and a tensile stress thereof concentrates so as to produce a relatively high tightening force on the baby's skin. Inconsequence, the baby's skin may be reddened and/or left with pressure traces. Meanwhile, if none of the front waist elastic members are arranged in the front waist region or the tensile stress of the front waist elastic members on the whole is set to a lower level in order to avoid the above described unfavorable condition, the fittability may be lowered and, in consequence, the wearing article may be displaced downward during use thereof.

An object of the present invention is to improve the conventional disposable wearing article, thereby providing a disposable wearing article wherein the front waist region has an appropriate fittability such that the front waist region may not tighten the lower abdominal region of the wearer.

Solution to Problem

To solve the object set forth above, the present invention is featured in a disposable article a having a vertical direction, a lateral direction intersecting with the vertical direction, a body facing surface and a non-body facing surface and including a front waist region, a rear waist region, a crotch region and a liquid absorbent structure extending to the front and rear waist regions centering on the crotch region.

In the disposable wearing article according to the present invention, the front waist region may have an upper edge partially defining a waist opening, a lower edge partially defining leg-openings, both lateral edges extending in the vertical direction between the upper and lower edges and a lower edge area extending in the lateral direction along the lower edge and an elastic strip located on the side of the body facing surface so as to extend in the lateral direction across the liquid absorbent structure between the both lateral edges of the front waist region along the lower edge area in the front waist region.

The elastic strip may have lateral fixed areas respectively located at the outside in the lateral direction of both lateral edges of the liquid absorbent structure and a free area defined between both lateral edges and the free area overlap with the liquid absorbent structure in planar view. In such wearing article, even in the area in which the liquid absorbent structure is present, the elastic parts of the elastic strip may be put in contact with the convexly curved underbelly to realize an appropriate folding force and fittability.

The wearing article further may include a central fixed area located between the lateral fixed regions and extending along the upper edge of the elastic strip. In such wearing article, a pocket adapted to absorb and contain body exudates may be defined between the free area of the elastic strip and the liquid absorbent structure.

The wearing article further including a waist layer located on the non-body facing surface wherein the waist layer may have an end flap extending across the liquid absorbent structure and the central fixed area of the elastic strip may be fixed to the end flap. In such wearing article applied on the wearer's body, the elastic strip may rise up from the central fixed area toward the wearer's body, and whereby the force to retain the elastic strip on the wearer's body may be increased and a sufficiently large pocket to contain body exudates may be defined between the elastic strip and the liquid absorbent structure.

The article further including a pair of barrier cuffs extending in the vertical direction at the outer side in the lateral direction of the liquid absorbent structure and the lateral fixed areas of the elastic strip may be fixed to the end flap. In such wearing article, the pocket opening may be largely formed and it is possible to keep the free area of the elastic strip in close contact with the wearer's body.

A dimension in the vertical direction of the elastic strip is at least 15 mm. In such wearing article, considering that a few month old baby often assumes a supine posture such as putting the toe in the mouth while lifting both legs with the buttocks and holding the toe, the elastic strip is located in the whole area being tucked or rolled up at the lower area in the front waist region in the vicinity of the lower abdominal region when worn. This makes it possible to lower a feeling of oppression due to concentration of a tensile stress on the lower side in the front waist region.

The upper edge of the elastic strip may lie in the lower side in the vertical direction of the front end edge of the liquid absorbent structure rather than in the front end edge of the liquid absorbent structure and the front waist region may include elastic members extending in the lateral direction across the central area of the liquid absorbent structure and these elastic members may be located on the side of the non-skin facing surface. In such wearing article, the elastic strip may cooperate with the elastic members to inhibit the deformation of the lower edge area in the front waist region.

The upper edge of the elastic strip may be located on the upper side of the front end edge of the liquid absorbent structure and the front waist region may have the elastic members extending in the lateral direction across the central area of the liquid absorbent structure and these elastic members may not be in overlapping relation with the elastic sheet in planar view. In such wearing article, a feeling of discomfort against the wearer due to the difference in level generated in the vicinity of the front end edge of the liquid absorbent structure may be reduced.

The wearing article may have an upper edge area located at the side of the waist-opening, an intermediate area located between the lower edge area and the upper edge area defined by trisecting the dimension in the vertical direction of the front waist region and a tensile stress in the lateral direction of the lower edge area per a given width is lower than the tensile stress in the lateral direction is lower than the tensile stress in the upper edge area as well as the tensile stress in the intermediate area. In such wearing article, the tensile stress of the lower edge area may be set to a relatively low level to prevent, even when a few month old baby changes the posture from a supine posture to a peculiar posture in which the baby lifts both legs with the buttocks, an excessive pressure should not build a feeling of pressure. Rather the elastic strip put in planar contact with the lower abdominal region may improve the appropriate fittability.

The tensile stress in the lateral direction per a given width of the upper edge area may be higher than the tensile stress in the lateral direction per a given width. In such wearing article, it is possible to put the front waist region in stable contact with the wearer's body at the side of the waist opening.

The tensile stress in the lateral direction of the lower edge area may be in a range of 0.4 N/35 mm to 0.7 N/35 mm. In such wearing article, the elastic strip may be kept in soft contact with the body such that the elastic strip may wrap around the lower abdominal region rather than compressing this region.

The front end of the liquid absorbent structure may have a deformation inducing parts extending in the vertical direction and the deformation inducing parts may be arranged at the outside in the vertical direction of the elastic strip. In such wearing article, even the liquid absorbent structure having a relatively high stiffness may smoothly be deformed so as to conform to the body, the freedom degree of the elastic strip itself may also be improved and, in this manner, the appropriate fittability may be brought to realization.

Advantageous Effects of Invention

With the disposable wearing articles according to one or more embodiments of the present invention, on the side of the body facing surface, the elastic strip may extend in the lateral direction along the lower edge area in the front waist region between both lateral edges of the front waist region across the liquid absorbent structure. In this way, the elastic strip may be put in soft contact with the wearer's lower abdomen which is most stable region in the abdomen, thereby inhibiting the displacement of the diaper during use.

BRIEF DESCRIPTION OF DRAWINGS

The drawings illustrate specific embodiments of the present invention, including optional and preferred embodiments as well as essential features of the invention.

DESCRIPTION OF EMBODIMENTS

The embodiments described below relate to a disposable wearing article illustrated in FIGS. 1 through 9, including both optional and preferred features as well as these features which are essential features of the present invention. Meanwhile, for convenience of description, a contour of a liquid absorbent member 22 is shown by a heavy line in FIGS. 2, 4, 7(a), 7(b) and FIG. 8.

Referring to FIG. 1 through FIG. 4, a disposable diaper 10 illustrated as an example of disposable wearing articles according to the present invention may include a body facing surface, a non-body facing surface opposed to the body facing surface, an annular elastic waist panel 11 extending in a waist circumference direction, an absorbent panel 20 joined to the elastic waist panel 11, a front waist region (one first and second waist regions) 13 and a rear waist region (the other first and second waist region) 14 and a crotch region 15 located between the front and rear waist regions 13 and 14. The diaper 10 is formed symmetrically about a vertical center line P-P bisecting a dimension of the diaper 10 in a lateral direction X thereof and the elastic waist panel 11 may be constructed of a front waist panel 30 defining the front waist region 13 and a rear waist panel 40 defining the rear waist region 14.

The front and rear waist panels 30 and 40 may respectively have a laterally long rectangular shape defined by lower edges 30a and 40a extending in the lateral direction X, upper edges 30b and 40b spaced apart from and opposed to the lower edges 30a and 40a in a vertical direction Y and both lateral edges 30c and 30d, and 40c and 40d extending in the vertical direction Y between the lower and upper edges 30a and 30b and between the lower and upper edges 40a and 40b, respectively. The lower and upper edges 30a and 30b, and 40a and 40b and the both lateral edges 30c and 30d, and 40c and 40d of the front and rear waist panels 30, 40 may correspond to lower and upper edges and both lateral edges of the front and rear waist regions 13 and 14, respectively.

Both lateral edges of the front waist panel 30 (i.e., both lateral edges of the front waist region 13) and both lateral edges (i.e., both lateral edges of the rear waist region 14) may respectively be overlapped with one another and joined together along respective rows of side seams 16 continually extending in the vertical direction Y to define a waist opening 18 and a pair of leg openings 19. The side seams 16 may be formed by well-known joining means, for example, various heat sealing means such as heat embossing/debossing or ultrasonic processing.

<Front Waist Panel>

Figure 1:
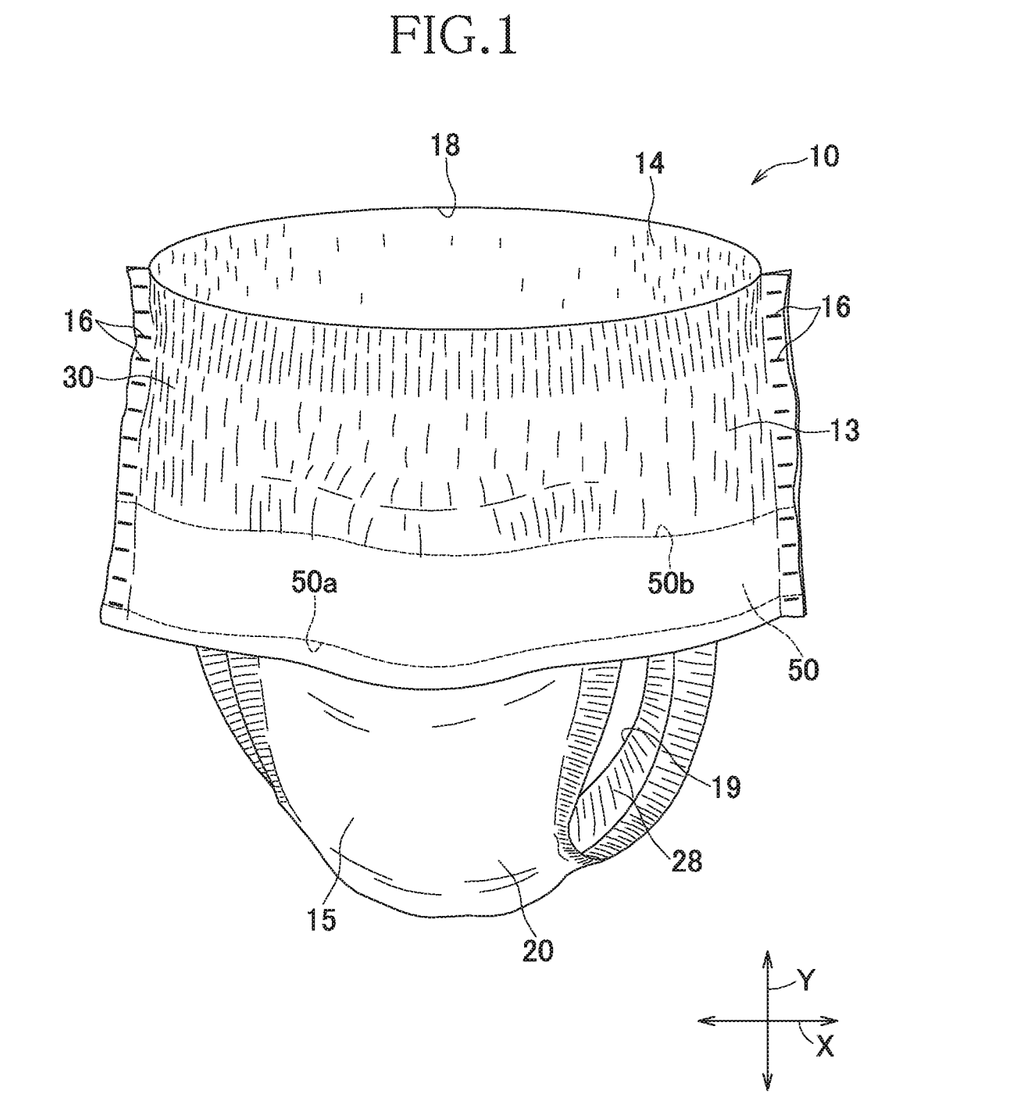
FIG. 1 A front perspective view of a disposable diaper according to a first embodiment as an example of the disposable wearing article according to the present invention.
Figure 2:
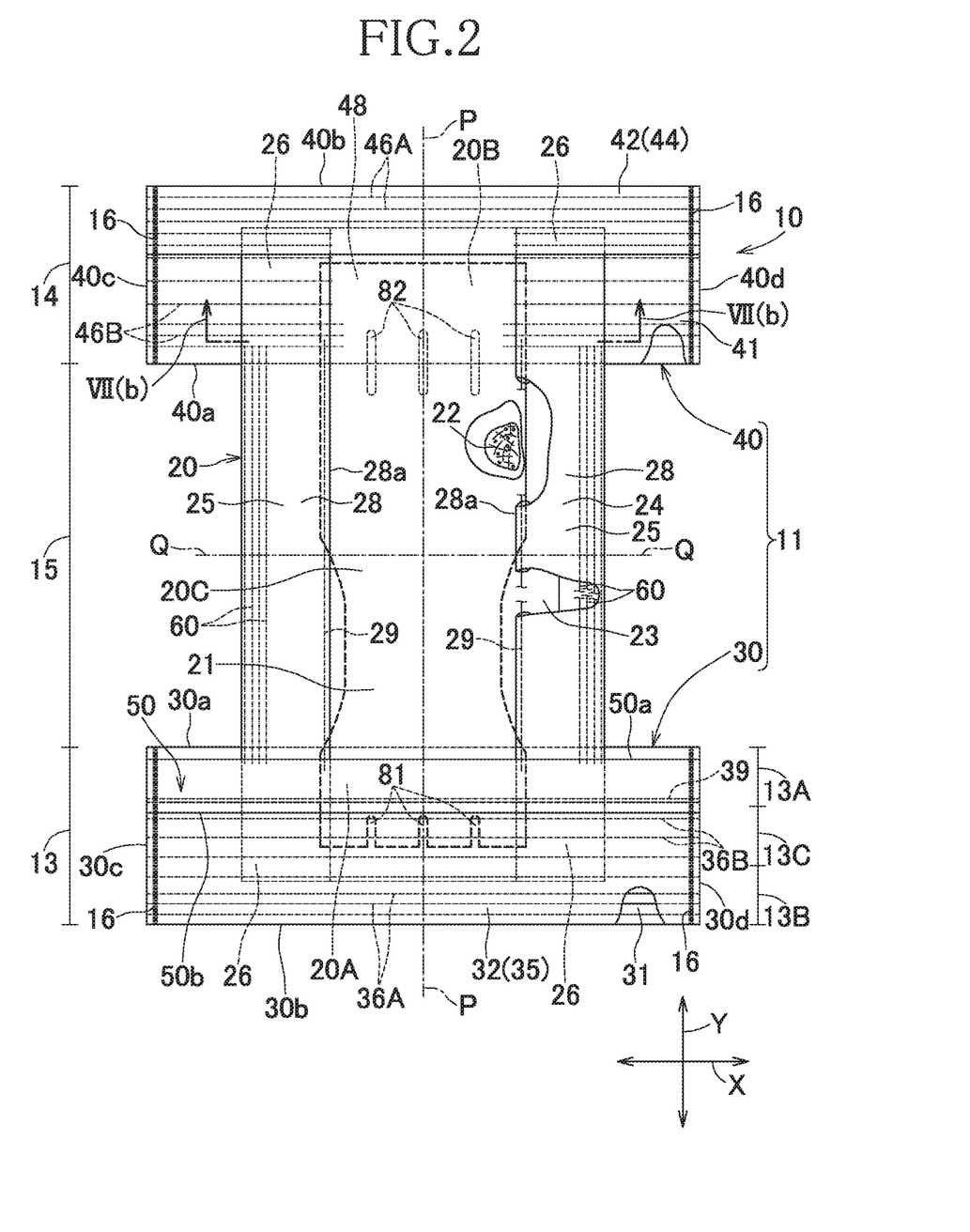
FIG. 2 A partially cut away developed plan view of the diaper developed in a vertical direction and in a lateral direction to the extent of the maximum elongation of respective elastic members (to the extent that gathers due to contractile force of elastic materials substantially disappear).
Figure 3:
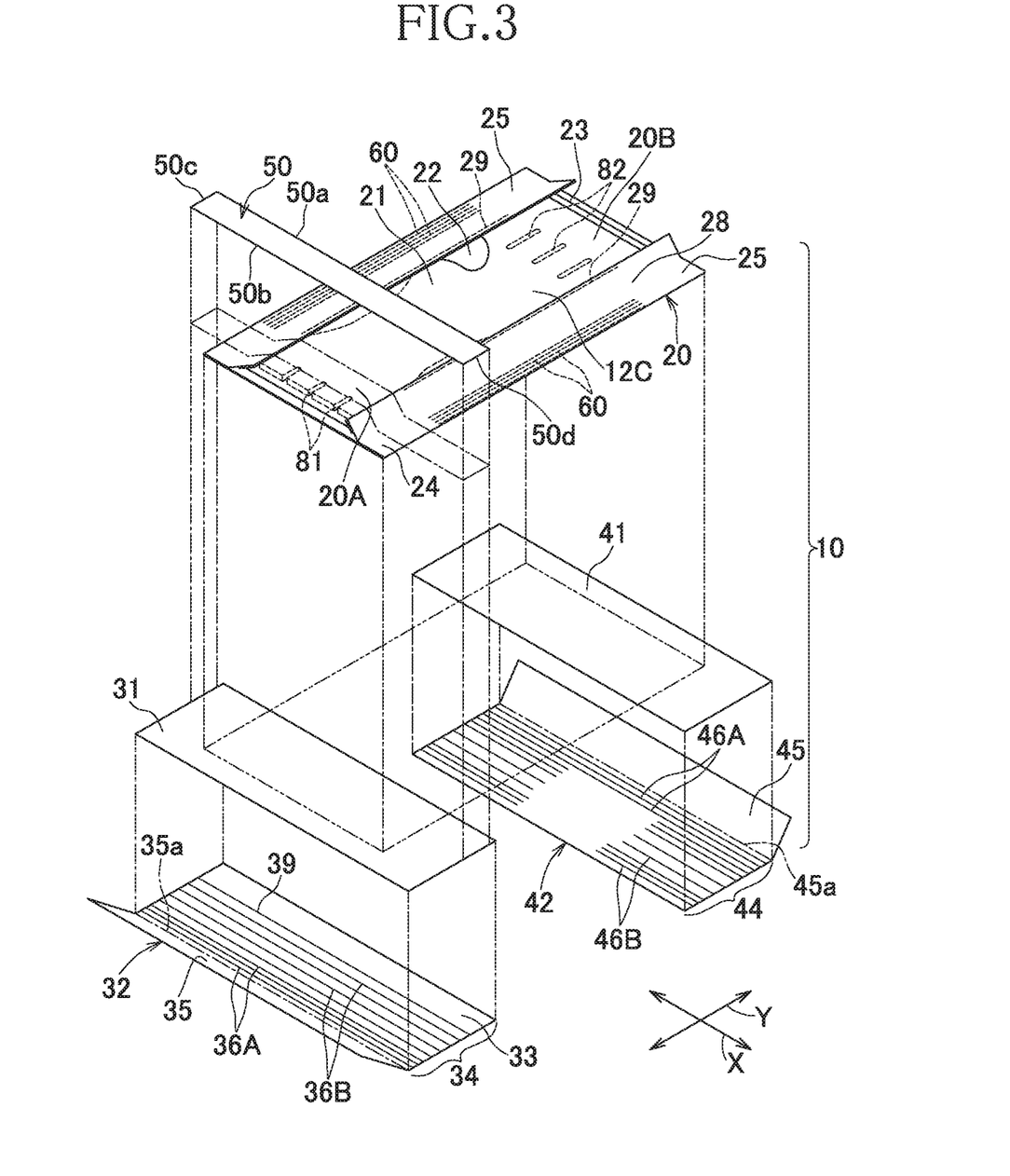
FIG. 3 A partially cut away exploded perspective view of the diaper.

With reference to FIGS. 2 and 3, the front waist panel 30 may include an interior layer 31 lying on the body facing surface and an exterior layer 32 lying on the non-body facing surface. The exterior layer 32 may have a main portion 34 fixed to the interior layer 31 and a folded portion 35 lying on the upper side of front end 20A of the absorbent panel 20 as viewed in the vertical direction Y. The portion 35 may be folded inward in the vertical direction Y along a fold line 35a extending in the lateral direction X and fixed to the interior surface of the lower edge 20A of the absorbent panel 20. Between the interior layer 31 and the main portion 34 of the exterior layer 32, a plurality of thread-like, strand-like or string-like front waist elastic members 36 may be arranged in a contractible manner under tension in the lateral direction X.

The front waist elastic members 36 may include a plurality of upper front waist elastic members 36A extending in the lateral direction X along the upper edge 30b so as to be located on the upper side in the vertical direction Y of the front end edge of the absorbent panel 20 and a plurality of lower front waist elastic members 36B extending in the lateral direction X across the absorbent panel 20 and a liquid absorbent structure 22 lying therein. Contraction of these elastic members 36A, 36B causes a plurality of gathers to be formed on the exterior surface of the front waist panel 36. In the front waist region 13, the lowermost one 39 of the lower front waist elastic members 36B lying on the side closest to the crotch region 15 is spaced from the inner end edge 30a.

Adjoining to the crotch region 15, an elastic strip 50 extending in the lateral direction X between both lateral edges 30c and 30d may be located on the body facing surface of the front waist region 13. The front waist region 13 may have the upper edge (i.e., the upper edge of the front waist panel) 30b, the lower edge (i.e., the lower edge of the front waist panel) 30a partially defining the leg opening edges and both lateral edges extending in the vertical direction Y (i.e., both lateral edges of the front waist panel) 30c and 30d. For convenience of description, the front waist region 13 is divided, in the vertical direction Y, into a lower edge area 13A extending in the lateral direction X along the lower edge 30a, an upper edge area 13B extending in the lateral direction X along the lower edge 30b and an intermediate area 13C extending in the lateral direction X between the lower edge area 13A and the upper edge area 13B. While the front waist region 13 is trisected in the vertical direction Y, the trisected areas may respectively have a dimension in the vertical direction Y which are different from one another.

In this regard, when the front waist region 13 has a dimension L1 in the vertical direction Y in a range of about 80 mm to about 120 mm, it is preferable that the respective dimensions in the vertical direction Y of the lower edge area 13A, the intermediate area 13C and the upper edge area 13B are in a range of about 20 mm to about 40 mm.

As materials for the elastic strip 50, for example, elastic fibrous nonwoven fabrics having a mass per unit area in a range of 15 g to 50 g. More specifically, well-known elastic nonwoven fabrics such as spun bonded fibrous nonwoven fabrics, melt blown fibrous nonwoven fabrics, heat roll fibrous nonwoven fabrics, SMS fibrous nonwoven fabrics, air laid fibrous nonwoven fabrics or air through fibrous nonwoven fabrics may be used in isolation or in combination to obtain the elastic strip 50. The elastic nonwoven fabrics may be formed from elastomer resins, for example, of polyethylene series or polyurethane series or thermoplastic resins such as polyethylene, polypropylene, polyester or acrylic.

<Rear Waist Panel>

The rear waist panel 40 may have an interior layer 41 lying on the body facing surface and an exterior layer 42 lying on the non-body facing surface. The exterior sheet 42 may have a main portion 44 joined to the interior layer 41 and a foldable portion 45 lying on the upper side of a rear end 20B of the absorbent panel 20 as viewed in the vertical direction Y. The foldable portion 45 may be folded inward in the vertical direction Y along a fold line 45a extending in the lateral direction X and fixed to the body facing surface of the interior layer 41. Between the interior layer 41 and the main portion 44 of the exterior layer 42, a plurality of thread-like, strand-like or string-like rear waist elastic members 46 may be arranged in contractible manner under tension.

The rear waist elastic members 46 may have a plurality of upper rear waist elastic members 46A arranged on the upper side in the vertical direction Y of the upper edge of the absorbent panel 20 so as to extend in the lateral direction X along the upper edge 40b and a plurality of lower rear waist elastic members 46B arranged on the lower side in the vertical direction Y of the upper rear waist elastic members 46A so as to extend in the lateral direction X from both lateral edges 40c and 40d of the rear waist region 14 to both lateral edges of the liquid absorbent structure 22. None of the lower rear waist elastic members 46B are arranged in an area overlapping with the central area of an absorbent core and such area in which none of the lower rear waist elastic members 46B define an inelastic region. Namely, the rear waist region 14 may have an upper elastic area in which the upper rear waist elastic members 46A are arranged, a pair of lower elastic areas each including the lower rear waist elastic members 46B spaced apart from and facing the lower rear waist elastic members 46B in the other lower elastic area, and an inelastic area 48 defined between the pair of lower elastic areas. Contraction of these elastic members may cause a plurality of gathers to be formed on the exterior surface of the rear waist panel 40.

As materials for the interior and exterior layers 31 and 41, and 32 and 42 of the front and rear waist panels 30 and 40, for example, spun bond fibrous nonwoven fabrics, SMS (spun bonded/melt blown/spun bonded) fibrous nonwoven fabrics, air-through fibrous nonwoven fabrics, each having a mass per unit area in a range of about 10 $g/m^2$ to 40 $g/m^2$ and a fiber density in a range of about 0.03 $g/cm^3$ to about 0.1 g/cm³ or plastic sheets or laminate sheets thereof may be used. As materials for the upper front and rear waist elastic members 36A, 46A, for example, elastic threads having a fineness of about 310 dtex to about 620 dtex and secured at an elongation ratio of 2.2 to 2.9 may be used. As materials for the lower front and rear waist elastic members 36B and 46B, for example, elastic threads having a fineness of about 310 dtex to about 620 dtex and secured an elongation ratio of about 2.2 to about 3.7 may be used. In addition, the elongation ratio and the fineness of the front and rear waist elastic members 36 and 46 may be appropriately varied deepening on the elastic force preset on each of the elastic areas.

<Absorbent Panel>

With reference to FIGS. 2 and 3, the absorbent panel 20 may have the front end 20A in the front waist region 13, the rear end 20B in the rear waist region 14 and an intermediate area 20C extending in the vertical direction Y between the front and rear ends 20A and 20B so as to define the crotch region 15. The absorbent panel 20 may have a bodyside liner 21 on the body facing surface and constructed of liquid permeable fibrous nonwoven fabrics, the liquid absorbent structure 22 having curved both lateral edges, a liquid impermeable leakage barrier layer 23 covering at least the entire bottom surface of the liquid absorbent structure 22, and a liquid impermeable covering layer 24 defining the entire non-body facing surface of the liquid absorbent panel 20. The liquid absorbent structure 22 may additionally include the absorbent core formed from a mixture of fluff wooden pulp and superabsorbent polymer particles or other absorbent materials and a liquid diffusive core wrapping sheet (not shown), for example, tissue paper, serving to wrap the core materials as a whole.

The covering layer 24 may include both barrier cuffs 25 formed of both lateral sides thereof. Both barrier cuffs 25 may respectively be folded inward and have front and rear ends 26 fixed to the interior surface of the leakage barrier layer 23 and the interior surface of the bodyside liner 21, both proximal edges fixedly extending in the vertical direction Y between the front and rear ends 26, and free parts 28 located medially in the lateral direction X to the both proximal edges. Each of the free parts 28 may have a tube-like distal edge 28a within which a plurality of thread-like, string-like and strand-like cuff elastic members 29 may be secured in contractible manner under tension in the vertical direction Y. Contraction of the cuff elastic members 29 may cause the free parts 28 to space away from the bodyside liner 21 toward the wearer's body, to be put in close contact with the wearer's thighs, thereby preventing from leaking sideways. Each of the barrier cuffs 25 may be arranged with a plurality of thread-like, string-like or strand-like leg-elastic members 60 arranged adjacently to the proximal edges in contractible manner under tension in the vertical direction Y. While the barrier cuffs 25 may be formed by the covering layer 24, the barrier cuffs 25 may be formed by liquid impermeable sheets separated from the covering layer 24.

Figure 4:
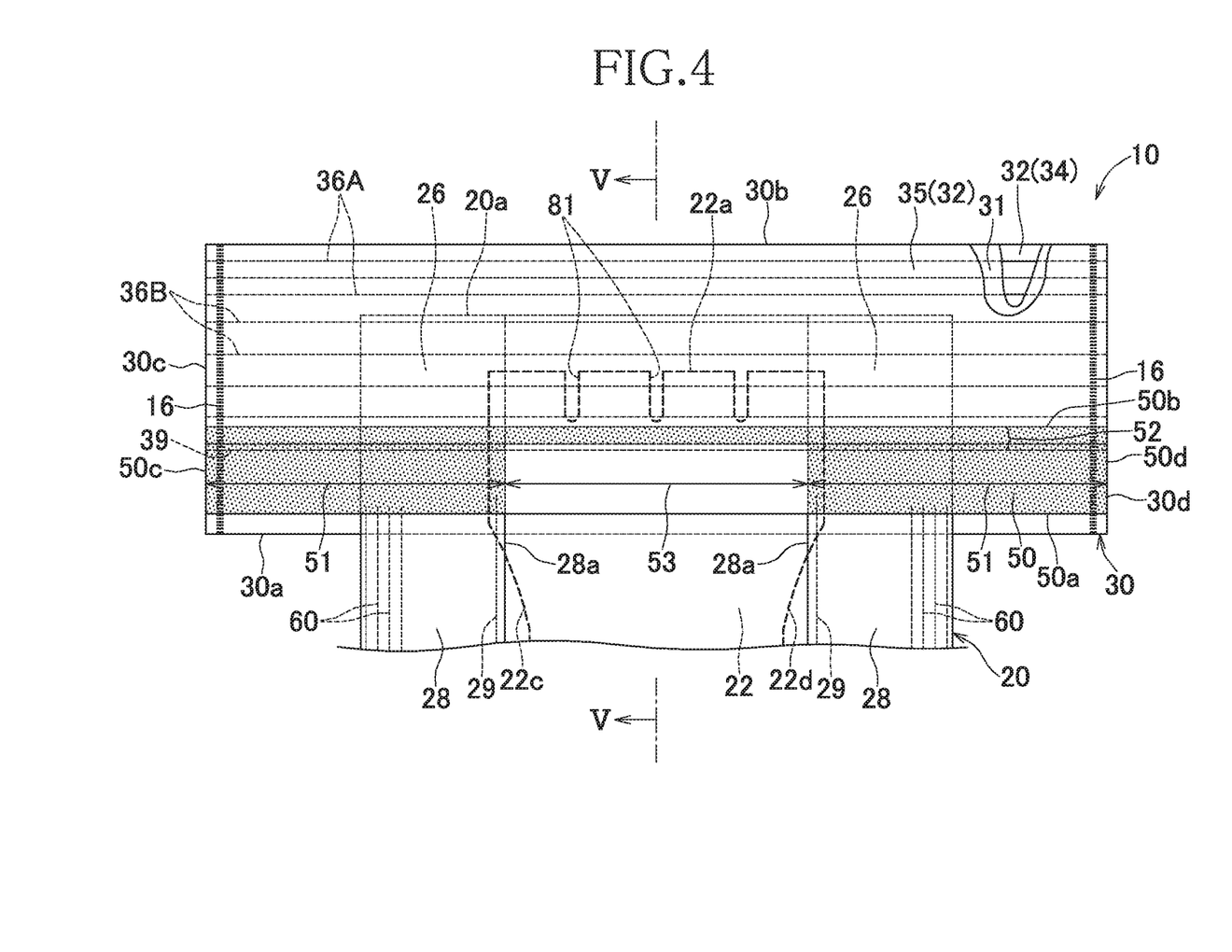
FIG. 4 A scale enlarged view of a front waist region.

With reference to FIGS. 2 through 4, the liquid absorbent structure 22 may have a plurality of slit or slot-like first and second deformation inducing parts 81 and 82 arranged in the front and rear ends or adjacently thereto so as to extend in the vertical direction Y and to be spaced apart from one another in the lateral direction X. The first deformation inducing parts 81 located in the front end of the liquid absorbent structure 22 may extend from the rear end edge of the liquid absorbent structure 22. The second deformation inducing parts 82 may be located inward in the vertical direction Y from the rear end edge 22b of the liquid absorbent structure 22 and extend vertically from the rear waist region 14 across the lower edge 40a toward the crotch region 15. So long as it is possible for the first and second deformation inducing parts 81 and 82 to deform the front and rear ends of the liquid absorbent structure 22 as desired, the number of the respective deformation inducing parts 81 and 82 may be one or three or more formed as slit (s) in which the liquid absorbent structure 22 is partially non-existent or as based concave groove(s) thinner than the parts other than the first and second deformation inducing parts 81 and 82.

In FIG. 4, for convenience of description, a contour line of the liquid absorbent structure 22 is shown by thick lines and fixed regions 51 and 52 of the elastic strip 50 are colored by a plurality of dilute dots. With reference to FIGS. 2, 3 and 4, the elastic strip 50 on the body facing surface of the lower edge area 13A of the front waist region 13 may be located at the upper side in the lateral direction X of the both lateral edges 22c and 22d of the liquid absorbent structure 22. Specifically, the elastic strip 50 may have a pair of the lateral fixed areas 51 extending from the both lateral edges 30c and 30d of the front waist region 13 to the distal edge 28a of the barrier cuffs 25, the central fixed region 52 extending along an upper edge 50b between the lateral fixed regions 51 and a free area 53 defined by the lateral fixed areas 51 and the central fixed area 52. By locating the elastic strip 50 on the body facing surface of the lower edge area 13A of the front waist region 13, the elastic band-like zone elasticized in the lateral direction X may be defined along the lower edge area 13A.

Figure 5:
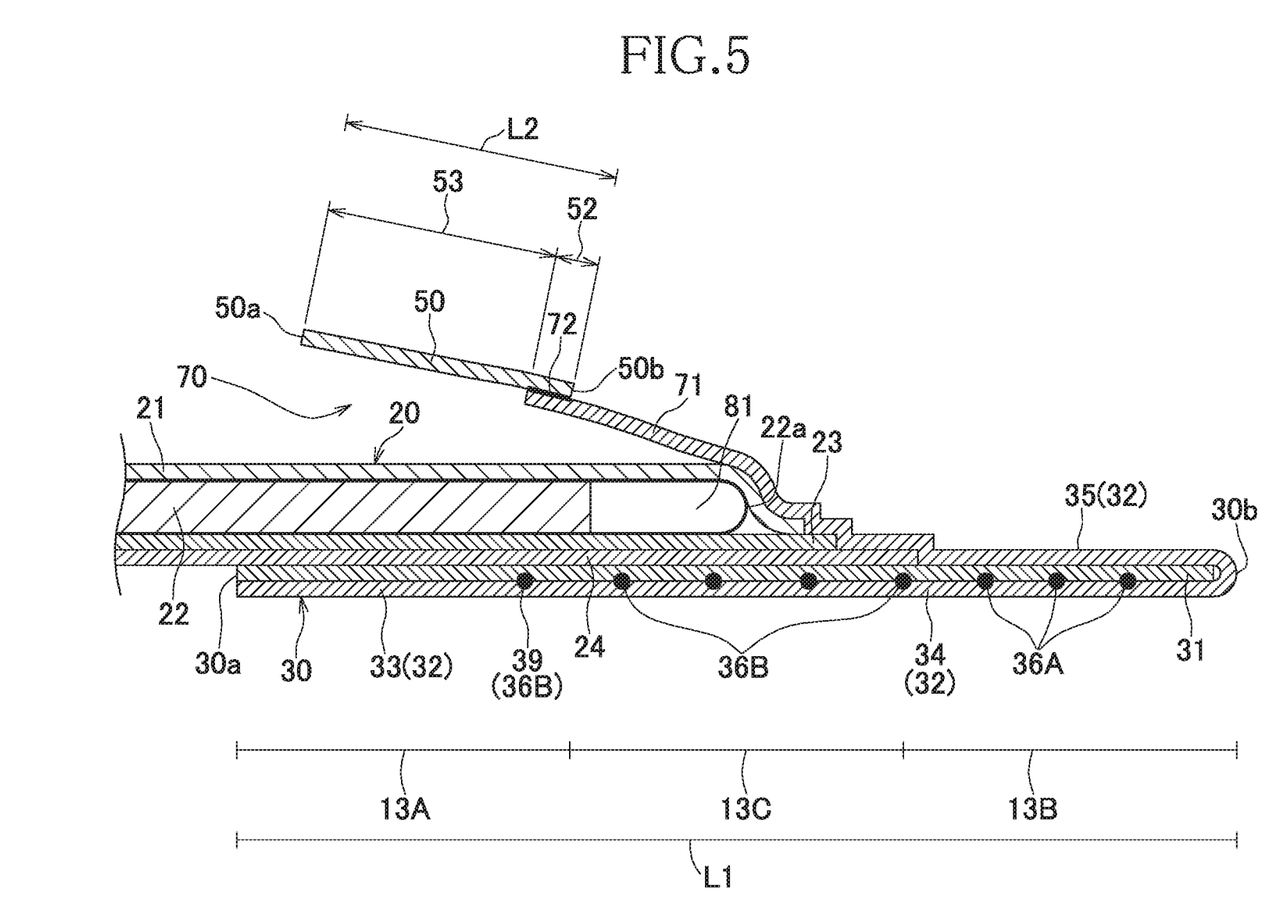
FIG. 5 A sectional view taken along line V-V in FIG. 4.

With reference to FIGS. 4 and 5, the free area 53 of the elastic strip 50 may be located between the distal edges 28a of the barrier cuffs 25. Between the bodyside liner 21 and the free area 53, a pocket 70 may be defined. In this manner, the elastic strip 50 may have the lateral fixed areas 51, the central fixed area 52 at the upper side in the vertical direction Y of the free area 53 while extending along the upper edge 50b, and the pocket 70 adapted to receive and contain body exudates.

The exterior layer 32 may have an end flap 71 located between the distal edges 28a of the barrier cuffs 25 without being fixed to the absorbent panel 20 and extending in the lateral direction X over the liquid absorbent structure 22. The central fixed area 52 of the elastic strip 50 may overlap the end flap 71 of the folded portion 35 and fixed thereto by the jointing area 72 coated with hot melt adhesive. The central fixed area 52 of the elastic strip 50 and the end flap 71 of the folded portion 35 of the exterior sheet 32 are fixed to each other so as to overlap each other in planar view. In consequence, in the diaper applied on the wearer's body, the free area 53 of the elastic strip 50 may be spaced away obliquely upward from the folded portion 35 of the exterior layer 32 toward the wearer's body as viewed in FIG. 5. In this way, an appropriate fittability may be improved compared to when the free area 53 is in parallel to the liquid absorbent structure 22. In addition, a space defined between the free area 53 and the bodyside liner 21 may communicate with a space defined between the free flap 71 and the bodyside liner 21 while extending upward in the vertical direction Y from the former space to define a relatively large space making it possible to contain a relatively large amount of body exudates. In the present preferred embodiment, the central fixed area 52 may be fixed to the outer surface of the folded portion 35 of the exterior sheet 32 and vice versa, and the lateral fixed area 51 of the elastic stripe 50 may be fixed to the lower edge area 13A of the front waist region 13, to overlap the elastic strip 50 on the folded portion 35, and whereby the pocket 70 may be defined.

The elastic strip 50 may be joined in the manner as described above and consequently the free area 53 may be located so as to overlap with the liquid absorbent structure 22 in planar view of the diaper 10. Generally, a lower abdominal region of the wearer having a convex forward shape makes it difficult for a liquid absorbent structure having a relatively high stiffness to extend along such convex lower abdominal region, and thus a gap may be left between the lower abdominal region and the liquid absorbent structure and lower the fittability. According to the present preferred embodiment, the elastic strip 50 is not joined to the liquid absorbent structure 22 but the elastic strip 50 on the interior surface of the liquid absorbent structure 22 may planarly be put in contact with the lower abdominal region. This makes it possible for the elastic strip 50 to exert an appropriate holding power (retaining force) against the wearer's body as well as to give a feeling of fitting. In addition, since a contractile force of the elastic strip 50 may not act directly upon the liquid absorbent structure 22, it is possible to inhibit the deformation of the liquid absorbent structure 22, for example, in the form of gathering which may cause the leakage of body exudates absorbed by the liquid absorbent structure 22.

The lateral fixed area 51 of the elastic strip 50 may be fixed to the free parts 28 of the barrier cuffs 25 (i.e., both lateral sides of the covering layer 24). Consequently, in the diaper applied on the wearer's body, the free area 53 between the lateral fixed areas 51 of the elastic strip 50 may also be spaced apart from the bodyside liner 21 when the cuff elastic members 29 are stretched and the free parts 28 of the barrier cuffs 25 may arise themselves up so as to be spaced away from the bodyside liner 21. This makes it possible to widely open the pocket 70 to receive body exudates smoothly. In addition, since the opening end edge of the pocket 70 may be defined by the elastic strip 50 formed of elastically stretchable material, even when the opening end edge is subjected to a force generated, for example, by the wearer's body movement and tending to deform or close the opening end edge, it is possible for the contractile force of the opening end edge to maintain the opened state of the pocket 70 against the above described force.

The pocket 70 formed in such manner makes it possible to collect body exudate reliably and, in addition, rise up of the barrier cuffs may make the free area 53 of the elastic strip 50 forming the pocket 70 to space away from the bodyside liner 21 so that the free region 53 may always be kept in contact with the wearer's body during use of the diaper. In this way, it is possible to maintain the lower edge area 13A as a whole in planar contact with the wearer's body and to ensure a comfortable texture compared to when an inelastic material different from the elastic strip is kept in contact with the wearer's skin.

The elastic strip 50 may extend in the lateral direction X along the lower edge 30a of the front waist region 13 and the lower edge 50a may slightly be spaced apart in the vertical direction Y from the lower edge 30a so as to be located on the upper side in the vertical direction Y of the lower edge 30a. So long as it is possible to achieve the technical effects of the present preferred embodiment, the lower edge 50a of the elastic strip 50 may extend in the lateral direction X at unity with the lower edge 30a of the front waist region 13 or may further extend in the vertical direction Y beyond the lower edge 30a.

Figure 6:
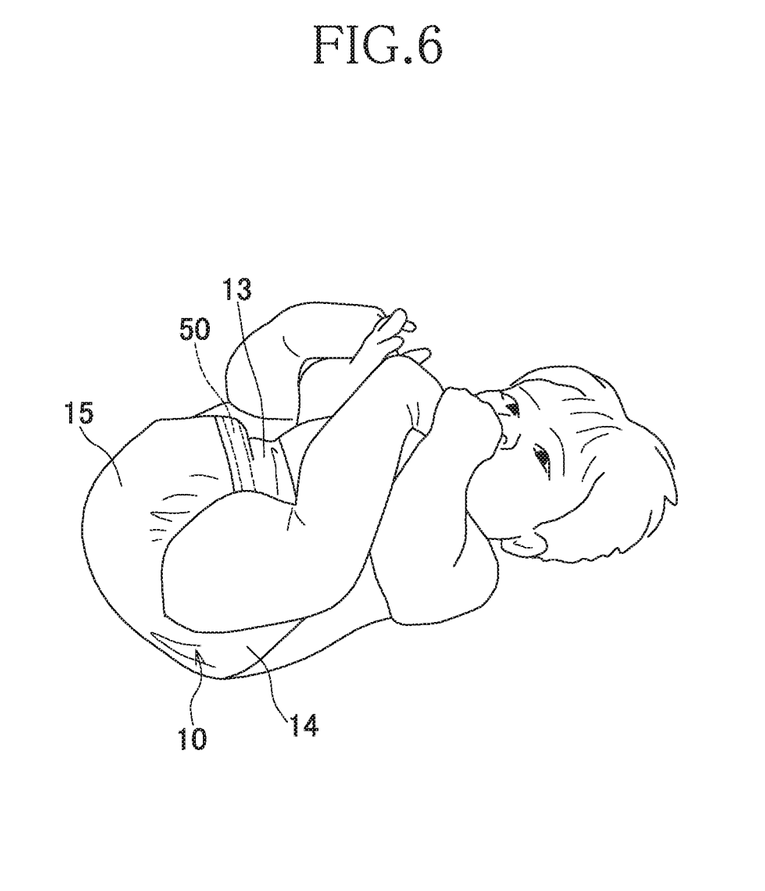
FIG. 6 A graphic illustrating a few month old baby having the diaper put thereon and lying in a spine posture.

For the wearer who is a few month old baby, excessive tightening on the lower abdominal region for the purpose of improving the fittability often makes the wearer feel uncomfortable. In addition, when tensile stress of a plurality of front waist elastic members arranged on the lower edge of the front waist region facing the lower abdominal region is relatively high, the wearer may be unwilling for the diaper to be applied on. For example, as illustrated in FIG. 6, the few month old baby sometimes assumes a supine posture such as putting the toe in the mouth while lifting both legs with buttocks. In such peculiar posture, if the front waist region includes a plurality of front waist elastic members arranged in its lower edge, these front waist elastic members may be brought together in this lower edge and a tensile stress thereof may concentrate so as to produce a relatively high tightening force on the wearer's skin. In consequence, the baby's skin may be reddened and/or printed with compression marks. Meanwhile, if none of the front waist elastic members is arranged in the front waist region or the tensile stress of the front waist elastic members on the whole is set to a lower level in order to avoid the above described unfavorable condition, the fittability may be lowered and, in consequence, the wearing article may be displaced downward during use thereof.

In the diaper 10 according to the present preferred embodiment, none of the thread-like, string-like or strand-like elastic members may be arranged in the lower edge area 13A of the front waist region 13 but the elastic strip 50 formed of stretchable material may be located therein. In consequence, the lower edge area 13A may softly be put in contact with the lower abdominal region of the wearer not only in the normal posture but also in the peculiar posture as has described above. In addition, the thread-like, strand-like or string-like front waist elastic members 36 arranged in the upper and intermediate areas of the front waist-region 13 except the lower edge area 13A, namely, in the upper edge area 13B and the intermediate area 13C enables these areas 13B and 13C to have the desired holding force (retaining force) and cooperate with the rear waist elastic members 46 arranged in the rear waist region 14 to put the diaper in stable contact with the wearer's waist and thereby to prevent the diaper from being displaced during use thereof.

when a belt-like elastic strip having a tensile stress lower than that of the thread-like, strand-like or string-like elastic materials is kept in contact with mesogarstrium swelling out and deflating during breathing or drinking and eating, and if the belt-like elastic strip to conform to the movement of the mesogarstrium, a gap may be formed between the front waist region and the wearer's body. However, the elastic strip 50, both lateral edges 50c and 50d may be located on the both lateral edges of the front waist region 13 and continuously extend in the lateral direction X so that the elastic strip 50 may be put in soft contact planarly with an area extending, from an area in the vicinity of one of the hipbones including the most stable bony framework in the baby's lower body, via the lower abdominal region through the mesogarstrium having less movement compared to the mesogarstrium, to the other hipbone. In consequence, the diaper 10 should not be displaced even if the tensile stress of the lower edge area 13A is relatively low.

With reference again to FIGS. 4 and 5, according to the present preferred embodiment, the upper edge 50b of the elastic strip 50 is located on the lower side, in the vertical direction Y, of the front end edge 22a of the liquid absorbent structure 22 and the non-body facing surface of the elastic strip 50 overlaps the lowermost front waist elastic member 39 extending in the lateral direction X across the central area of the liquid absorbent structure 22 in planar view. When the wearer is in the peculiar posture as illustrated in FIG. 6, the lower edge area 13A may be pinched between the thighs and deformed so as to float off from the wearer's body. However, the elastic sheet 50 cooperates with the single lowermost front waist elastic member 39 made of single thread-like, strand-like or string-like elastic materials to develop a contractile force sufficient to inhibit the deformation of the lower edge area 13A. In addition, the lowermost front waist elastic member 39 may planarly overlap the joining area 72 in which the central fixed area 53 of the elastic strip 50 and the end flap 71 of the folded portion 35 are fixed to each other. In the joining area 72, the elastic strip 50 and the exterior sheet 32 may be overlapped and joined to each other so as to define a flexion point at which the area defining the pocket 70 may be deformed. In view of this, the lowermost front waist elastic member 39 may be located on such flexion point to restrict a degree of the flexion, thereby inhibiting the degradation of the available space serving to contain body exudates.

With reference to FIG. 5, a dimension in the vertical direction Y (width dimension) L2 of the elastic strip 50 is preferably at least 15 mm and more preferably 25 mm to 35 mm. When the dimension L1 of the lateral edge of the front waist region 13 may be in a range of about 100 mm to 120 mm, it will be possible to put the elastic strip 50 in soft contact with the wearer's lower abdominal region of the wearer without giving the wearer a feeling of oppression.

The front waist region 13 that a tensile stress in the lateral direction X of the lower edge area 13A is preferably lower than the tensile stress in the lateral direction X of the upper edge area 13B and the intermediate area 13C. As illustrated in FIG. 6, even when a few month old baby wearing the diaper in supine posture assumes a peculiar posture lifts both legs with the buttocks, the lower abdominal region should not be compressed because the tensile stress of the lower edge area 13A may be relatively low and the elastic strip 50 may function to wrap around the lower abdominal region with an appropriate holding force, thereby ensuring a good fit-on feeling.

The tensile stress in the lateral direction X over a given width in the vertical direction Y of the upper edge area 13B is preferably higher than a tensile stress in the lateral direction X per a given width of the intermediate area 13C. Such correlation of the tensile stress between the upper edge area 13B and the intermediate area 13C makes it possible to put the front waist region 13 in relatively close contact to the wearer's body around the waist opening and to put the intermediate area 13C in contact with the abdominal region at an appropriate fittability without compressing the abdominal region.

Specifically, a tensile stress in the lateral direction X per a given width (per 35 mm) in the vertical direction Y of the lower edge area 13A is preferably 0.4 N/35 mm to 0.7 N/35 mm, a tensile stress in the lateral direction X per the given width of the upper edge area 13B is preferably 0.8 N/35 mm to 1.0 N/35 mm, and a tensile stress in the lateral direction X per the given width of the intermediate area 13C is preferably 0.6 N/35 mm to 0.9 N/35 mm.

<Measurement of Tensile Stress>

Measurement of tensile stress in the respective area of the front waist region 12 were measured by using a tensile tester (for example, AUTOGRAPH Tensile Tester (AG-1KNI) in the form of cycle testing.

First, three test pieces were cut out along cut lines trisecting a vertical dimension of the front waist region 13 (i.e., a length dimension from the waist upper edge 30b to the lower edge 30a). Specifically, an area (test piece 1) located on the side of the waist opening 14, an area located on the side of the leg openings 19 (test piece 2) and an area located between these two areas (test piece 3) were cut out. Thereafter, a spacing dimension between lower edges of each pair of the adjacent side seams 16 (dimension in the lateral direction) in the respective test pieces was measured in the state of the respective test pieces stretched until the gathers disappeared to obtain a width dimension W1 as a measurement value at the moment of the maximum elongation. After the respective test pieces have been left for 48 hours or longer under atmospheric condition at a temperature of 20° C., each of the respective test pieces in contracted condition was set by jigs. More specifically, one of the side seam areas 16 was fixed by stationary jig (chuck) and the other of the side seam areas 16 was attached to movable jig (chuck). The test piece set in this manner was stretched in the direction in which the test piece should be stretched (lateral direction X) at a rate of 100 mm/min until a distance between the chucks attained to 90% of the width dimension W1. Then the distance between the chucks was reversed (inverted) at a rate of 100 mm/min to 90% of the width dimension W1 and by converting the measurement values to values per width 35 mm to obtain the values of tensile stress (N/35 mm) of the respective test pieces.

As the result of trisecting the dimension L1 in the vertical direction Y of the front waist region 13 in the measurement as described above, the tensile stress in the lateral direction X of the leg opening area (test piece 1) including the skin-side elastic sheet 50 was 0.4 N/35 mm to 0.7 N/35 mm, the tensile stress in the lateral direction X of the region on the side of the waist opening was 0.8N/35 mm to 1.0 N/35 mm, and the tensile stress in the lateral direction X of the region (test piece 3) lying between the above described areas was 0.6 N/35 mm to 0.9 N/35 mm.

Figure 7A:
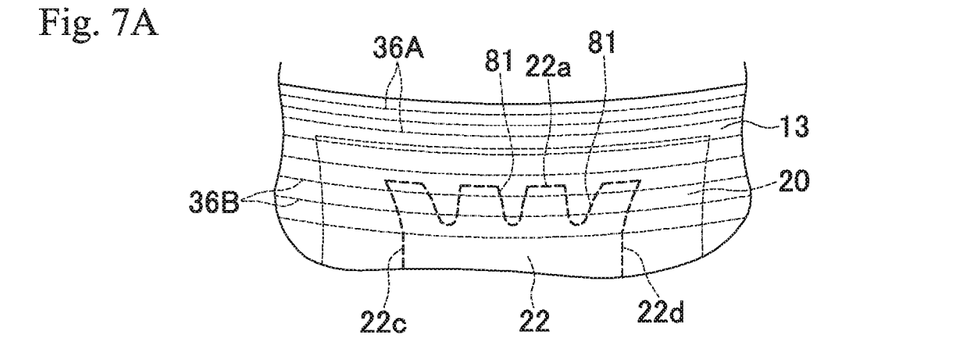
FIG. 7A A graphic illustrating a front end portion of a liquid absorbent structure in the diaper put on the wearer's body and FIG. 7B a sectional view taken along line VII (b)-VII(b) in FIG. 2 of the diaper put on the wearer's body.

With reference to FIG. 7A, the front end of the liquid absorbent structure 22 is curved along the abdominal region of the wearer under an effect of the deformation inducing parts 81. In this manner, a plurality of the deformation inducing parts 81 make it possible to deform the liquid absorbent structure 22 having a relatively high stiffness along the abdominal region, thereby improving a freedom degree of elasticity of the elastic strip 50 located on the interior side of the liquid absorbent structure 22 and improving the fittabilty to the wearer's body. In addition, when the wearer is a few month old baby generally having a body shape characterized in a convexly bulgy mesogastrium, the intermediate area 13C adapted to be put in contact with the mesogastrium may be convexly expanded and, in consequence, the cutouts defined by the deformation inducing parts 81 may be enlarged in the lateral direction X. In this way, the dimension in the lateral direction of the front end portion of the liquid absorbent structure 22 may be enlarged by the deformation inducing parts 81 and, in consequence, the intermediate area 13C may be stretched along the shape of the mesogastrium at a degree higher than stretching rates of the lower and upper edge areas 13A and 13B without that the mesogastrium may be firmly compressed.

Figure 7B:
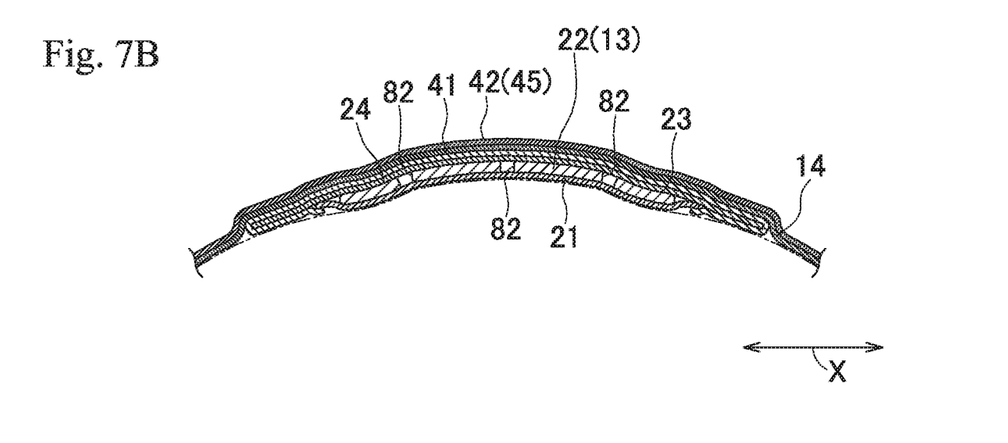

With reference to FIG. 7B, in the rear waist region 14, the deformation inducing parts 82 extending in the vertical direction Y are located in the rear end portion of the liquid absorbent structure 22 so that the rear end may be curved along the wearer's buttocks and the fittability may be improved.

While, according to the present preferred embodiment, the elastic stripe 50 may be located in the lower edge area 13A of the front waist region 13, it is possible to locate the elastic strip formed of elastic materials also in the lower area of the rear waist region 14 adapted to face the lower edge area 13A as viewed in a front-back direction of the diaper 10.

Second Embodiment

Figure 8:
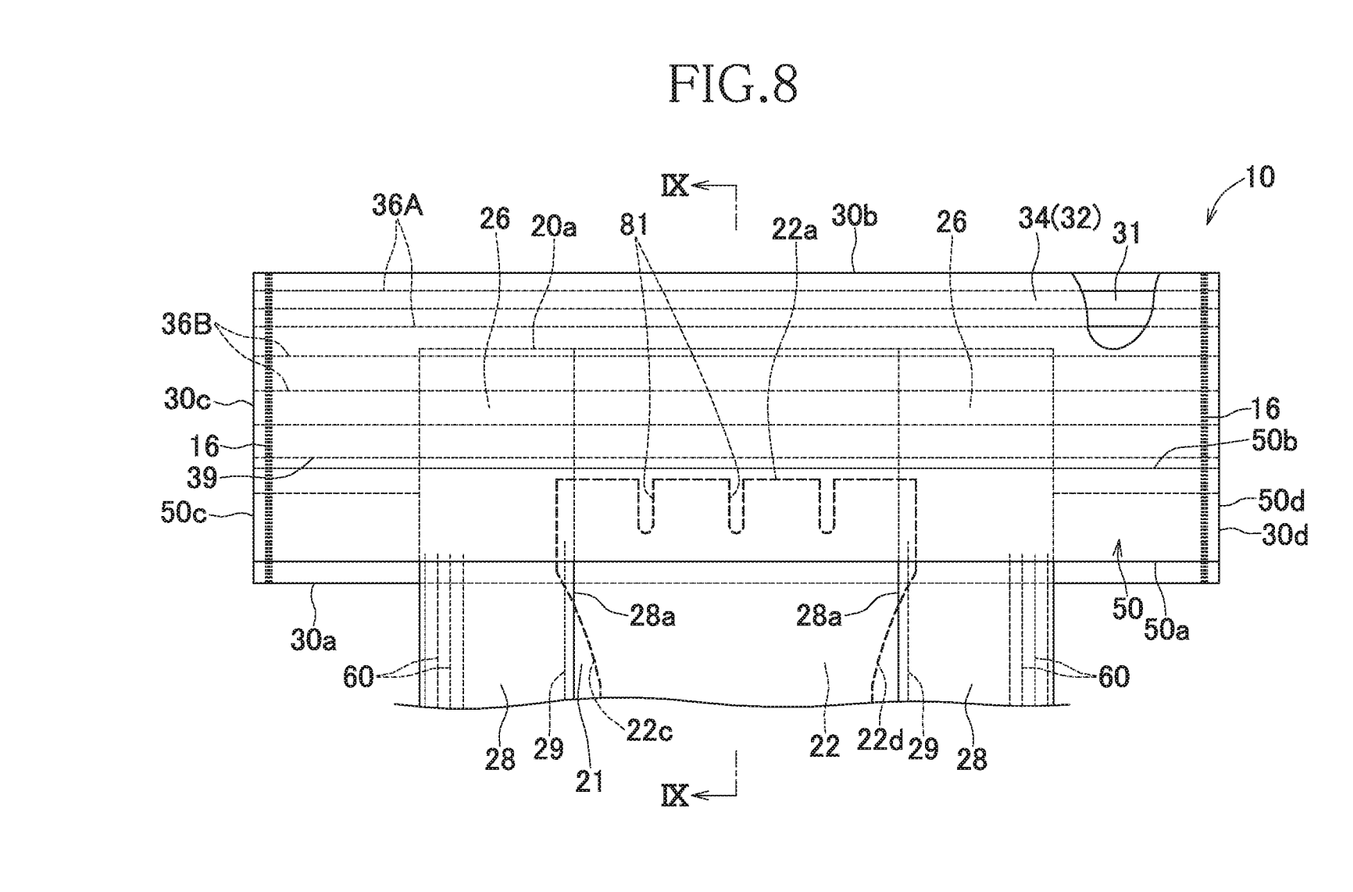
FIG. 8 A plan view similar to FIG. 4 illustrating a diaper according to a second embodiment.
Figure 9:
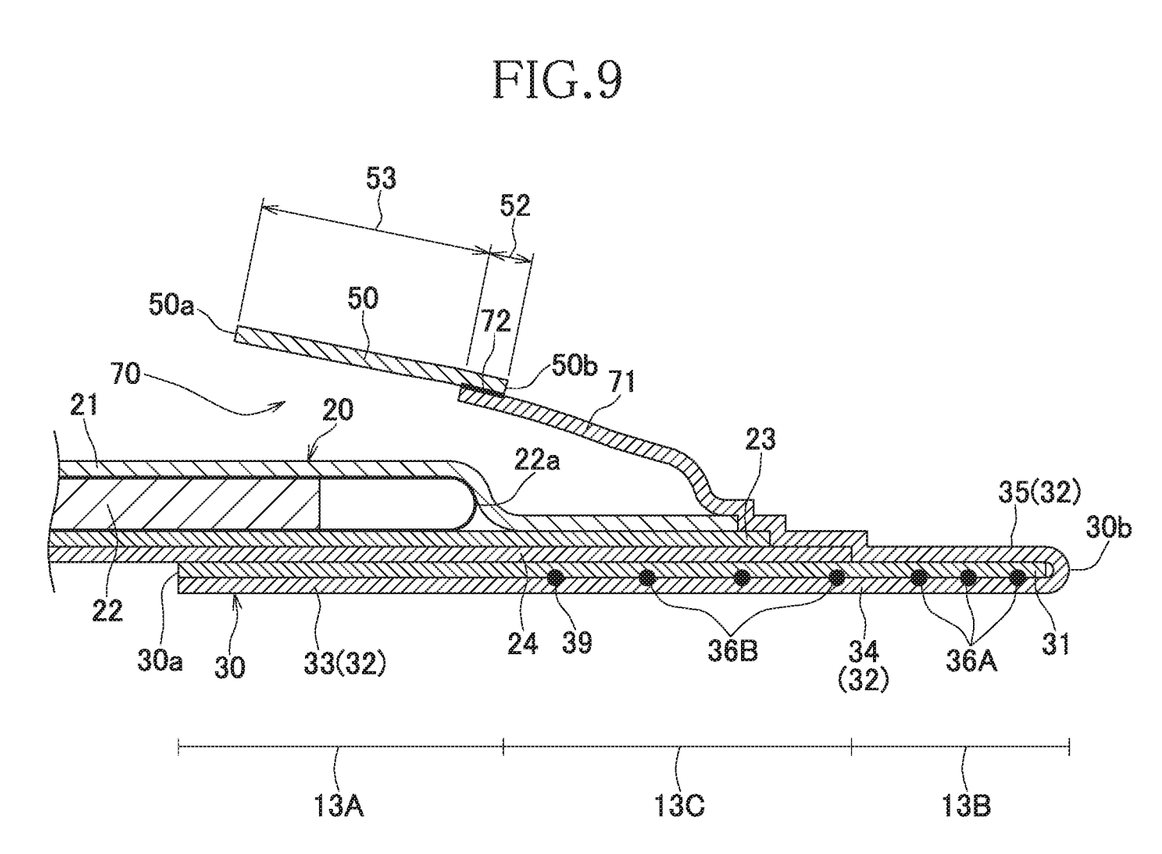
FIG. 9 A sectional view taken along line IX-IX in FIG. 8.

FIG. 8 is a plan view similar to FIG. 4, of the front waist region 13 of the diaper 10 according to a second embodiment and FIG. 9 is a sectional view taken along line IX-IX in FIG. 8. A basic arrangement of the diaper 10 according to the present embodiment is similar to that of the diaper 10 according to the first embodiment and therefore the description given hereunder is limited to a point of differences.

With reference to FIGS. 8 and 9, in the diaper 10 according to this preferred embodiment, the upper edge 50b of the elastic strip 50 may located on the upper side of the front end edge 22a of the liquid absorbent structure 22. The liquid absorbent structure 22 may have a thickness dimension and stiffness larger and higher than those of the sheet member and, therefore, an uneven thickness dimension in the vicinity of the front end edge 22a may define an unevenness making the wearer have a sense of discomfort. However, it is possible to restrict such sense of discomfort for the wearer by covering the front end portion (or a part thereof) including the front end edge 22a of the liquid absorbent structure 22.

The elastic strip 50 and the lower front waist elastic members 36B (i.e., the lowermost front waist elastic member 39) do not overlap each other in planar view. None of the thread-like, strand-like or string-like elastic members may be located in the lower edge area 13A of the front waist region 13 and only the elastic strip 50 may be located herein to elasticize this lower edge area 13A so that the entire lower edge area 13A may be put in soft contact with the wearer's lower abdomen without that the wearer may suffer from an oppressive feeling and compression marks may be left on the wearer's skin.

The construction members of the diaper 10 are not limited to those described in the specification but other various types of materials widely used in the relevant technical field may be used without limitation unless otherwise stated. As used herein, the terms "first", "second" or the like used in the present specification are merely to distinguish the similar elements, similar parts or the other similar matters. While the present specification describes the technical effect achieved chiefly when the diaper 10 is put on few month old babies, the unique arrangement of the diaper 10 according to the present invention may have advantageous effects for wearers of wide range from children of walking age to elderly adults.

The invention claimed is:

1. A disposable wearing article having a vertical direction, a lateral direction intersecting with the vertical direction, said disposable wearing article comprising:
    a body facing surface and a non-body facing surface,
    a front waist region,
    a rear waist region,
    a crotch region, and
    a liquid absorbent structure extending to the front and rear waist regions and centering on the crotch region, said liquid absorbent structure having an absorbent core, wherein
    the front waist region is divided into, in the vertical direction
        a lower edge area extending in the lateral direction along a lower edge of the front waist region,
        an upper edge area extending in the lateral direction along an upper edge of the front waist region, and
        an intermediate area between the lower edge area and the upper edge area and extending in the lateral direction,
    the front waist region includes a plurality of front waist elastic members in the upper edge area and the intermediate area, the plurality of front waist elastic members extending in the lateral direction between both lateral edges of the front waist region,
    the lower edge area has an elastic strip extending in the lateral direction between the both lateral edges of the front waist region and located on a side of the body facing surface of the liquid absorbent structure,
    the elastic strip is located only in the front waist region of the front and rear waist regions, and is not located in the upper edge area of the front waist region, and
    a part of the plurality of front waist elastic members and the elastic strip extends across the absorbent core.

2. The wearing article according to claim 1, wherein the elastic strip has
    lateral fixed areas respectively located at an outer side in the lateral direction of both lateral edges of the liquid absorbent structure, and
    a free area defined between the lateral fixed areas and overlapping the liquid absorbent structure in a planar view of the wearing article.

3. The wearing article according to claim 2, wherein the elastic strip further has a central fixed area located between the lateral fixed areas and extending along an upper edge of the elastic strip.

4. The wearing article according to claim 3, further comprising a waist layer located on a side of the non-body facing surface,
    wherein the waist layer has an end flap extending across the liquid-absorbent structure and the central fixed area of the elastic strip is fixed to the end flap.

5. The wearing article according to claim 4, wherein a lowermost front waist elastic member, among the plurality of front waist elastic members, in the planar view of the wearing article, overlaps a joining area in which the central fixed area of the elastic strip and the end flap of the waist layer are fixed with each other.

6. The wearing article according to claim 2, further comprising a pair of barrier cuffs extending in the vertical direction at the outer side in the lateral direction of the liquid absorbent structure, wherein the lateral fixed areas of the elastic strip are fixed to free parts of the barrier cuffs.

7. The wearing article according to claim 1, wherein a dimension of the elastic strip in the vertical direction is at least 15 mm.

8. The wearing article according to claim 1, wherein
    an upper edge of the elastic strip is lower than a front end edge of the liquid absorbent structure in the vertical direction rather than in the front end edge of the liquid absorbent structure, and
    the plurality of front waist elastic members extend across a central area of the liquid absorbent structure and are located on a side of the non-body facing surface.

9. The wearing article according to claim 1, wherein
    a lower edge of the elastic strip is located on an upper side of a front end edge of the liquid absorbent structure in the vertical direction, and
    the plurality of front waist elastic members extend across a central area of the liquid absorbent structure and are not in overlapping relation with the elastic strip in a planar view of the wearing article.

10. The wearing article according to claim 1, wherein a tensile stress in the lateral direction of the lower edge area per a given width is lower than the tensile stress in the lateral direction of the upper edge area and lower than the tensile stress in the lateral direction of the intermediate area.

11. The wearing article according to claim 10, wherein the tensile stress in the lateral direction per a given width of the upper edge area is higher than the tensile stress in the lateral direction per a given width of the intermediate area.

12. The wearing article according to claim 10, wherein the tensile stress in the lateral direction of the lower edge area is in a range of 0.4 N/35 mm to 0.7 N/35 mm.

13. The wearing article according to claim 1, wherein a front end of the liquid absorbent structure has deformation inducing parts extending in the vertical direction and the deformation inducing parts are arranged lower than the elastic strip in the vertical direction.

14. A disposable wearing article having a vertical direction, a lateral direction intersecting with the vertical direction, body facing surface and non-body facing surface and including a front waist region, a rear waist region, a crotch region, a liquid absorbent structure extending to the front and rear waist regions centering on the crotch region, and a pair of barrier cuffs, wherein:
the front waist region has an upper edge partially defining a waist opening, a lower edge partially defining leg openings, both lateral edges extending in the vertical direction between the lower and upper edges and a lower edge area extending in the lateral direction along the lower edge,
an elastic strip located on the side of the body facing surface so as to extend in the lateral direction across the liquid absorbent structure between the both lateral edges of the front waist region along the lower edge area in the front waist region, and
the pair of barrier cuffs extends in the vertical direction at the upper side in the lateral direction of the liquid absorbent structure and the lateral fixed area of the elastic strip is fixed to free parts of the barrier cuffs.

15. A disposable wearing article having a vertical direction, a lateral direction intersecting with the vertical direction, body facing surface and non-body facing surface and including a front waist region, a rear waist region, a crotch region and a liquid absorbent structure extending to the front and rear waist regions centering on the crotch region, wherein:
the front waist region has an upper edge partially defining a waist opening, a lower edge partially defining leg openings, both lateral edges extending in the vertical direction between the lower and upper edges and a lower edge area extending in the lateral direction along the lower edge,
an elastic strip located on the side of the body facing surface so as to extend in the lateral direction across the liquid absorbent structure between the both lateral edges of the front waist region along the lower edge area in the front waist region,
the lower edge of the elastic strip is located on the upper side of the front end edge of the liquid absorbent structure, and
the front waist region has the elastic members extending in the lateral direction across the central area of the liquid absorbent structure and these elastic members are not in overlapping relation with the elastic strip in planar view.

* * * * *